US010615523B2

(12) United States Patent
Henschel

(10) Patent No.: US 10,615,523 B2
(45) Date of Patent: Apr. 7, 2020

(54) BATTERY BRIDGE AND METHOD FOR ACTIVATING AN ELECTRONIC DEVICE

(71) Applicant: BIOTRONIK SE & Co. KG, Berlin (DE)

(72) Inventor: Martin Henschel, Berlin (DE)

(73) Assignee: BIOTRONIK SE & Co. KG, Berlin (DE)

(*) Notice: Subject to any disclaimer, the term of this patent is extended or adjusted under 35 U.S.C. 154(b) by 727 days.

(21) Appl. No.: 15/399,317

(22) Filed: Jan. 5, 2017

(65) Prior Publication Data

US 2017/0222338 A1 Aug. 3, 2017

(30) Foreign Application Priority Data

Jan. 29, 2016 (DE) .................. 10 2016 101 620

(51) Int. Cl.
*H01R 11/01* (2006.01)
*H01R 4/02* (2006.01)
(Continued)

(52) U.S. Cl.
CPC .......... *H01R 11/01* (2013.01); *A61N 1/3758* (2013.01); *B23K 26/22* (2013.01); *B23K 26/242* (2015.10);
(Continued)

(58) Field of Classification Search
CPC .... H01R 11/01; H01R 43/0221; H01R 4/029; B23K 26/22; B23K 26/242; B23K 26/28;
(Continued)

(56) References Cited

U.S. PATENT DOCUMENTS 3,766,308 A 10/1973 Loro
4,990,741 A * 2/1991 Moores .............. B23K 26/0738
219/121.64
(Continued)

FOREIGN PATENT DOCUMENTS

DE         696 07 652 T2    10/2000
DE    10 2007 008 549 A1     8/2008
DE    10 2013 108 563 A1     2/2015

OTHER PUBLICATIONS

German Search Report for German Case No. DE 10 2016 101 620.9, dated Jul. 6, 2018 (10 pages).
(Continued)

*Primary Examiner* — Sherman Ng
(74) *Attorney, Agent, or Firm* — Buchanan Ingersoll & Rooney PC

(57) ABSTRACT

A battery bridge for an electronic device, preferably for an electronic implant, has an electrically conductive first contact element, an electrically conductive second contact element and an insulator. The first contact element and the second contact element comprise a weldable material. In a first state of the battery bridge, the first contact element is distanced from the second contact element via a predefined air gap and the first contact element is electrically insulated from the second contact element by the air gap and the insulator. The battery bridge is formed in such a way that it can be transferred, by welding the first contact element and the second contact element together, into a second state, in which the air gap between the first contact element and the second contact element is closed electrically conductively, at least in part. A method for activating such an electronic device is also disclosed.

12 Claims, 9 Drawing Sheets

(51) Int. Cl.
*H05K 3/32* (2006.01)
*B23K 26/22* (2006.01)
*H05K 1/02* (2006.01)
*B23K 26/32* (2014.01)
*H01R 43/02* (2006.01)
*B23K 26/28* (2014.01)
*B23K 26/242* (2014.01)
*A61N 1/375* (2006.01)
*H01M 2/20* (2006.01)
*B23K 101/38* (2006.01)
*H05K 3/40* (2006.01)
*H05K 3/22* (2006.01)
*B23K 101/36* (2006.01)

(52) U.S. Cl.
CPC ............ *B23K 26/28* (2013.01); *B23K 26/32* (2013.01); *H01M 2/204* (2013.01); *H01R 4/029* (2013.01); *H01R 43/0221* (2013.01); *H05K 1/0293* (2013.01); *H05K 3/328* (2013.01); *B23K 2101/36* (2018.08); *B23K 2101/38* (2018.08); *H05K 3/222* (2013.01); *H05K 3/4015* (2013.01); *H05K 2201/10053* (2013.01); *H05K 2201/10181* (2013.01); *H05K 2201/10242* (2013.01); *H05K 2201/10363* (2013.01); *H05K 2201/10583* (2013.01); *H05K 2203/107* (2013.01); *H05K 2203/173* (2013.01)

(58) Field of Classification Search
CPC ............ H05K 3/328; H05K 2203/107; H05K 2201/10583
USPC ...................................................... 174/68.1
See application file for complete search history.

(56) References Cited

U.S. PATENT DOCUMENTS

| | | | |
|---|---|---|---|
| 6,740,821 | B1 | 5/2004 | Jiang et al. |
| 7,781,696 | B2 * | 8/2010 | Schreiber ............. B23K 1/0008 219/121.64 |
| 9,259,805 | B2 * | 2/2016 | Kim ....................... B23K 26/402 |
| 2006/0222942 | A1 * | 10/2006 | Zhao ................... H01M 2/0473 429/180 |
| 2007/0298287 | A1 | 12/2007 | Tajima et al. |
| 2010/0326967 | A1 * | 12/2010 | Freitag ................... B23K 26/28 219/121.64 |
| 2013/0048363 | A1 | 2/2013 | Weng et al. |

OTHER PUBLICATIONS

European Search Report and Annex to the European Search Report on European Patent Application No. EP 17 15 1706.3, dated Jun. 22, 2017 (9 pages).

* cited by examiner

BATTERY BRIDGE AND METHOD FOR ACTIVATING AN ELECTRONIC DEVICE

CROSS-REFERENCE TO RELATED APPLICATIONS

This patent application claims the benefit of and priority to co-pending German Patent Application No. DE 10 2016 101 620.9, filed on Jan. 29, 2016 in the German Patent Office, which is hereby incorporated by reference in its entirety.

TECHNICAL FIELD

The present invention relates to a battery bridge for an electronic device, preferably for an electronic implant and also to a method for activating an electronic device of this type comprising an electric circuit.

BACKGROUND

A battery bridge is understood to mean the contact of an electric circuit of an electronic device that remains open last. If the open contact of the battery bridge is closed following assembly and testing of the electronic device, the device is thus activated, i.e., the electric circuit forming the basis of the device is permanently closed.

With regard to an electronic implant, correct activation is of course of particular importance, since lasting fault-free functioning of the implant must be ensured. By way of example, cardiac pacemakers, cardioverter defibrillators, electronic drug delivery devices, or implantable sensors (biomonitors) are currently used as electronic implants.

Due to the requirement that an electric circuit for electronic devices of this type should take up as little space as possible, said circuit is currently often produced by means of SMT (surface mounting technology). In the case of surface mounting technology, components are soldered directly onto a printed circuit board by means of solderable connection faces.

In order to activate an electronic device, a soldering method was used previously, for example, in which tin is applied by means of a soldering iron and closes the circuit between two adjacent soldering faces on the printed circuit board (PC board or PCB). The disadvantage of this conventional solution lies in the fact that soldering methods nowadays cannot be reliably automated in respect of the small structures as can be provided on highly compact circuits, since the soldering process is influenced by the solder amount, the soldering temperature, the fluxing agent, the cleanliness of the surfaces, and the like.

It is also known to keep a contact of the battery strip insulated by means of a temporary insulator until activation. Once the electronic device is finished, the contacts having been welded, the device is powered up via test points. Following successful power-up, the temporary insulator is manually removed; the battery strip, which has not yet been welded on, is manually held down and manually welded on by means of one to two weld points. This method has the disadvantage that the circuit must be activated by a complex power-up device, wherein a connection lug of the battery always has to be insulated via a temporary insulator. An accidental contacting of the strip (bounce of the contact) and therefore accidental initialization should be avoided as a result of this measure. It is also disadvantageous that in this method, following successful initialization of the circuit, the temporary insulator is manually removed from the battery connection strip, the strip is placed by means of tweezers on the circuit, and then must be welded on to the weld path. This complex manual process step is time-consuming and requires fine motor skills. It cannot be automated from the viewpoint of cost-effectiveness. In addition, additional material has to be provided, fed and positioned for the temporary insulator. The same is true for the connection strip.

An alternative solution lies in closing the circuit by means of a bonding method. For this purpose, material (for example, aluminum strip/wire) has to be fed, and the strip ends have to be welded on by means of friction welding or laser welding. The bonding method presupposes an already fixed internal structure of the electric circuit, for example, by gluing, on account of the high forces that occur as the strip is held down and welded on (resistance welding). However, this is problematic for electronic implants, since no adhesives can be used, so as to avoid a high expenditure of time for the curing of an adhesive and also adhesive evaporation, which can have a negative effect on the electronic behavior of the device.

A further alternative possible embodiment for a battery bridge could consist in closing the circuit by means of a plug-in contact. However, for electronic implants there is the requirement that the electronic circuit must operate reliably over the entire service life of the implant, that is to say up to 10 years. The material fatigue of the springs or contact resistances, which change over time, however, constitute a risk in respect of the product reliability. The use of plug-in contacts/spring contacts for electronic devices such as electronic implants therefore is not recommended.

The present invention is directed toward overcoming one or more of the above-mentioned problems.

SUMMARY

An object of the present invention thus lies in creating a battery bridge with which an electric circuit can be reliably activated in a simple, automatable manner. In respect of the method, an object is to specify a method which enables an activation of an electronic device in a simple and economical way.

At least the above object(s) is achieved by a battery bridge which has an electrically conductive first contact element, an electrically conductive second contact element, and an insulator, wherein the first contact element and the second contact element comprise a solderable material, wherein, in a first ("open") state of the battery bridge, the first contact element is distanced from the second contact element by a predefined air gap and the first contact element is electrically insulated from the second contact element by the air gap and the insulator, wherein the battery bridge is configured in such a way that it can be transferred, by welding the first contact element and the second contact element to one another, into a second ("closed") state, in which the air gap between the first contact element and the second contact element is permanently closed electrically conductively, at least in part.

By means of the battery bridge according to the present invention, in the second (closed) state, an electric circuit is closed and, therefore, the device comprising the circuit is activated. For this purpose, the material of the first contact element and the material of the second contact element are fused together in the region of the air gap by means of welding, such that on the one hand the weld seam or weld spot of the air gap is closed and on the other hand an electrically conductive connection is established between the first contact element and the second contact element.

The battery bridge according to the present invention must consist of weldable material, at least in the area of the contact elements in which the welding is performed by way of example, the first contact element and the second contact element can be made at least in part of at least one material of the group containing nickel, copper, copper-nickel alloys, copper, niobium, tanatalum, molybdenum, stainless steel, platinum alloys, palladium alloys, and titanium.

The air gap preferably has a width ranging from 10 µm to 100 µm, particularly preferably ranging from 30 µm to 80 µm. An air gap of this type on the one hand has the necessary insulating property in the first (open) state and on the other hand can be reliably closed electrically conductively by means of laser welding in order to produce the second (closed) state. In the first (open) state, the electronic device is not activated.

The insulator insulates the first contact element and the second contact element electrically from one another. However, the insulator also serves for the mechanical fastening of the first contact element and the second contact element. For this purpose, the insulator is preferably arranged either between the first contact element and the second contact element and is connected thereto, or the first contact element and the second contact element are arranged on the insulator and are fastened thereto.

The battery bridge according to the invention is characterized in that it can be economically produced and, by means of the welding process, also enables an automated activation of the electronic device. With the use of a battery bridge according to the present invention, the activation/initialization can therefore be performed in a narrow, automated manufacturing sequence.

It is also advantageous when the insulator is substantially annular, the first contact element is substantially U-shaped or hollow-cylindrical in cross-section, and the second contact element is substantially cylindrical, wherein the annular insulator is arranged between the first contact element and the second contact element. The U-shaped or hollow-cylindrical first contact element is also referred to as a cap, and the second cylindrical contact element is also referred to as a plunger. A rotationally symmetrical design of the components of this type means that these are automatically centered and the small insulation distance can thus be provided reliably along the entire welding edge. The insulator holds the electrically conductive, preferably metal, contact elements of the battery bridge in position and ensures the predefined air gap, which provides the insulation of the contact elements from one another. Accidental contact between the first contact element and the second contact element can thus be avoided. An arrangement of the components that is particularly advantageous in respect of the spatial requirement is given in that the second contact element is arranged, particularly preferably in a press fit, within an inner opening of the first contact element, which opening is preferably continuous.

It is also advantageous, in particular in respect of the above-explained rotationally symmetrical exemplary embodiment, when the first contact element and/or the second contact element are produced from a metal material by means of a cold forming or stamping process. The insulator can be embodied for example as a plastics injection-molded part, for example, comprising a material of the group containing POM (polyoxymethylene), PEEK (polyether ether ketone), LCP (liquid-crystal polymer), and PBT (polybutylene terephthalate), or as a film comprising a material of the group containing PEEK, polyimide, LCP and polyarylate.

In a further preferred exemplary embodiment the second contact element, preferably also the first contact element, has a sloped portion, which shields a laser light used for welding from an electric circuit, for example, a printed circuit board, arranged beneath the battery bridge. The sloped portion is characterized in that, in this portion, in particular with a rotationally symmetrical design of the first contact element or of the second contact element, the diameter of the corresponding contact element changes from a smaller diameter to a larger diameter, such that the contact element forms a sloping edge. Due to this sloped portion, the laser light is deflected and reflected in a direction away from an electric circuit disposed therebeneath, such that damage to the circuit caused by the welding of the first contact element to the second contact element is avoided.

In a further preferred embodiment, the first contact element and/or the second contact element have/has, in a portion serving for connection to the electric circuit, a coating which improves solderability and which for example contains gold (e.g., ENIG (electroless nickel immersion gold)) and/or palladium. As a result, the soldered connection of the battery bridge to corresponding contact faces of conductive tracks of a printed circuit board, for example, during surface mounting, is improved.

It is also advantageous when the second contact element, in the region of an upper end face of the first contact element, in which region the welding is performed, protrudes beyond this upper end face. Due to the shaping of the battery bridge according to the present invention, an improved welding in order to close the air gap between the first contact element and the second contact element is achieved, for example, by means of fillet welding. The produced weld seam can be easily examined in respect of its quality, i.e., the establishment of an electrically conductive connection between the first contact element and the second contact element.

In an alternative embodiment, compared to the U-shaped or cylindrical design of the first contact element and of the second contact element, the first contact element is formed as a first metal foil and the second contact element is formed as a second metal foil. The insulator is formed by a ceramic substrate. The first contact element and the second contact element are also arranged adjacently on the insulator at a distance corresponding to the width of the air gap. This exemplary embodiment can be produced particularly easily and economically, for example, by means of thick-film technology, wherein the air gap is preferably produced in that a continuous metal film resting on the ceramic substrate is separated, for example, by means of laser cutting. At the same time, the second metal foil distanced from the first metal foil is formed as a result. Electrically conductive contact with an electric circuit (printed circuit board, PCB) arranged therebeneath and comprising the first contact element or the second contact element is established in this embodiment by means of a soldering coating arranged laterally on the battery bridge, which coating spans, in a U-shaped manner, the ceramic substrate and preferably additionally the first contact element or second contact element resting thereon. A nickel intermediate layer is preferably arranged between the first contact element and the second contact element or the insulator and the soldering coating and serves to produce the solderability and wettability with soft solder.

The weldable metal foil of the first contact element and the second contact element can, for example, comprise at least one material of the group containing nickel, copper, copper-nickel alloys, tanatalum, niobium, molybdenum, titanium and stainless steel. The production is performed in a thick-film method, similarly to an industrially produced thick-film resistor (TFR). On account of the production by means of thick-film technology, a battery bridge according to this exemplary embodiment can be produced very efficiently and economically. The metal foil of the first contact element and/or of the second contact element by way of example has a layer thickness ranging from 200 µm to 600 µm. The dimensions of a battery bridge produced in accordance with this exemplary embodiment can be, for example, 2 mm×1.25 mm. This battery bridge according to the present invention is therefore characterized in addition to the above-mentioned properties by small dimensions and therefore by a small area requirement.

In a further alternative exemplary embodiment, the first contact element has a first shape and the second contact element has a second shape, which is complementary to the first shape, wherein the air gap is formed at or between the opposing faces of the first shape and the second shape and in a region is filled out by the insulator, which, for example, is formed as an adhesive film (for example, in the form of an acrylate adhesive). The first contact element and the second contact element are weldable metal components, for example, comprising a material of the group containing nickel, a copper-nickel alloy, and stainless steel. As complementary shape, an L-shape (in cross-section) can be used, for example. Other shapes, for example complementary wave shapes, are also conceivable.

The insulator formed as adhesive film and arranged in the region of part of the air gap between the two complementary shapes fixes the air gap between the first contact element and the second contact element. Since the first contact element and the second contact element extend as far as the underside of the battery bridge, they can each be directly connected to a contact face of an electric circuit (e.g., printed circuit board) arranged therebeneath. A battery bridge of this type measures, for example, 2 mm×1.25 mm in size and therefore has a small spatial requirement. The complementary shapes of the first and the second contact element of this exemplary embodiment can be produced by cold forming (e.g., stamping, embossing) or by material removal (e.g., milling, water jet cutting, etching).

A battery bridge of this type can preferably be provided with a housing produced by means of plastics injection molding. Here, however, the upper side of the battery bridge comprising the first contact element, the second contact element, and the air gap arranged therebetween is free, such that the air gap is accessible for welding at the time of activation of the electric circuit. The underside of the contact elements is also not covered by the housing, since this serves to establish contact with the electric circuit.

At least the above object(s) is also achieved by a method for activating an electronic device, preferably an electronic implant, comprising an electric circuit by means of an above-described battery bridge, said method having the following steps:

positioning and fastening the battery bridge in the first (open) state on the electric circuit and producing an electrically conductive connection between the first contact element and a first conductive track and also between the second contact element and a second conductive track of the electric circuit, wherein the connection to the first conductive track and/or the second conductive track is established preferably via a corresponding contact face, connecting the electric circuit to a voltage source and/or a capacitor and/or a dump resistor, powering up the electric circuit via at least two predefined test points, and transferring the battery bridge into the second (closed) state by at least partial welding of the first contact element and the second contact element to one another, in such a way that the air gap is permanently closed electrically conductively, at least in part.

The method according to the present invention includes an automatable welding process and, therefore, a greater process reliability. The run-through time for the power-up can thus be reduced. In the method according to the present invention, simpler manufacturing aids, for example, merely a workpiece carrier, can also be used, and no additional parts are fed or carried away, such that the course of the manufacturing process can be provided in a straightforward manner. The battery bridge according to the present invention or the method according to the present invention can therefore be used in particular in the production of electronic implants in the field of medical technology, in particular in cardiac pacemaker/ICD/biomonitor production.

A butt seam welding method, a fillet welding method or a through-welding method is preferably used for welding, depending on the shape of the air gap or of the first contact element and the second contact element.

Further embodiments, objectives, features, advantages and possible applications of the present invention will become clear from the following description of exemplary embodiments with reference to the drawings. Here, all features described and/or illustrated in the drawings form the subject matter of the present invention, independently or in any combination, even regardless of their summary in the claims and the dependency references of the claims.

DESCRIPTION OF THE DRAWINGS

This invention is explained in detail below on the basis of some sample embodiments. The figures are as follows.

DETAILED DESCRIPTION

Figure 1:
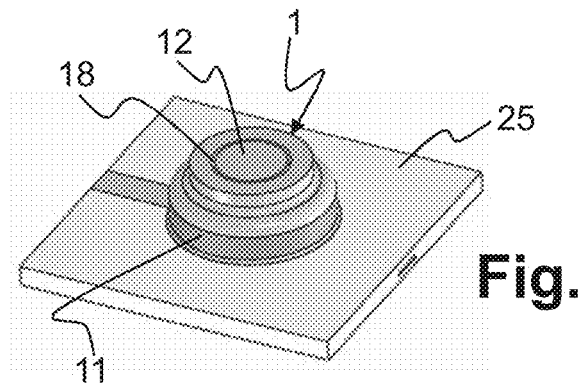
FIG. 1 schematically shows a first exemplary embodiment of a battery bridge according to the present invention in the first state connected to a printed circuit board, in a perspective view from the side, FIG. 2 schematically shows the arrangement according to FIG. 1 in cross-section, FIG. 3 schematically shows the exemplary embodiment according to FIG. 1 in an exploded illustration, in a view from the side, FIG. 4 schematically shows the arrangement according to FIG. 3 in cross-section, FIGS. 5-9 schematically show a first exemplary embodiment of a method according to the present invention for activating an electronic device comprising a battery bridge according to FIG. 1 in a number of steps, wherein a perspective view from the side is shown in FIGS. 5-7 and 9 and a sectional illustration is shown in FIG. 8, FIG. 10 schematically shows the arrangement according to FIG. 1 in cross-section, FIG. 11 schematically shows the arrangement according to FIG. 10 in a second state of the battery bridge, FIG. 12 schematically shows a second exemplary embodiment of a battery bridge according to the present invention in a first state, in a perspective view from the side, FIG. 13 schematically shows the exemplary embodiment according to FIG. 12 in cross-section during the welding, FIG. 14 schematically shows a third exemplary embodiment of a battery bridge according to the present invention in a first state, in a perspective view from the side, FIG. 15 schematically shows the exemplary embodiment according to FIG. 14 in cross-section during the welding, FIG. 16 schematically shows a fourth exemplary embodiment of a battery bridge according to the present invention in a perspective view from the side during the welding, FIG. 17 schematically shows a fifth exemplary embodiment of a battery bridge according to the present invention in a first state, in a perspective view from the side, connected to a printed circuit board, FIG. 18 schematically shows the arrangement according to FIG. 17 in cross-section, FIG. 19 schematically shows the arrangement according to FIG. 18 in a second state of the battery bridge, FIGS. 20-23 schematically show a second exemplary embodiment of a method according to the present invention for activating an electronic device comprising a battery bridge according to FIG. 17 in a number of steps, in each case in a perspective view from the side, FIG. 24 schematically shows a sixth exemplary embodiment of a battery bridge according to the present invention in a first state, in a perspective view from the side, connected to a printed circuit board, FIG. 25 schematically shows the arrangement according to FIG. 24 in a second state of the battery bridge, FIG. 26 schematically shows a seventh exemplary embodiment of a battery bridge according to the present invention in a first state, in a perspective view from the side, FIG. 27 schematically shows the arrangement according to FIG. 26 in a cross-section, FIG. 28 schematically shows the arrangement according to FIG. 26 in a second state, in a partial transparent illustration of the battery bridge, and FIG. 29 schematically shows an electronic device in the form of a cardiac pacemaker in cross-section including a circuit diagram with a battery bridge according to the present invention according to FIG. 1 in the first state.
Figure 2:
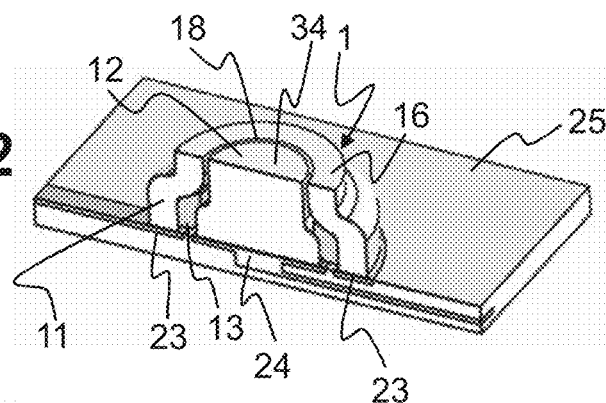
Figure 3:
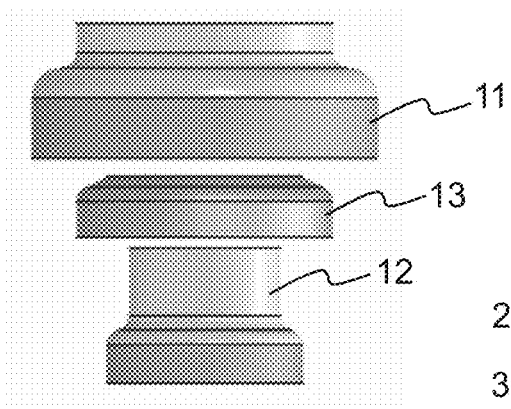

The first exemplary embodiment of a battery bridge 1 according to the present invention illustrated in FIGS. 1-11 has a substantially weldable hollow-cylindrical cap (first contact element) 11 and a weldable, substantially cylindrical plunger (second contact element) 12. A ring 13 (insulator) is also provided and is arranged between the cap 11 and the plunger 12. The plunger 12 and the ring 13 are arranged within the continuous opening 15 of the cap 11. The ring 13 provides a concentric positioning of the plunger 12 and cap 11 relative to one another, in such a way that an air gap 18 is formed therebetween. That air gap by way of example has a width of approximately 50 µm. In the first (open) state of the battery bridge illustrated in FIGS. 1-2, 5-6 and 10, the metal cap 11 and the metal plunger 12 are electrically insulated from one another by means of the electrically insulating ring 13 and the air gap 18. The plunger 12 has the same height as the cap 11, such that the upper end face 16 of the cap 11 and the upper end face 34 of the plunger 12 are flush with one another.

Figure 4:
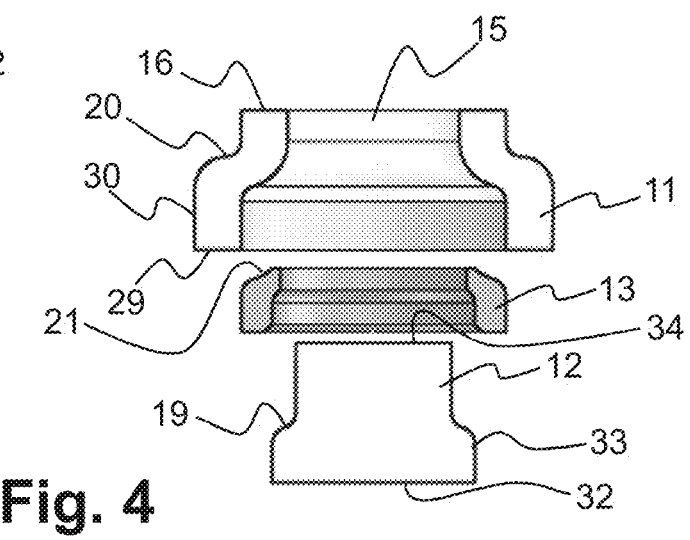
Figure 8:
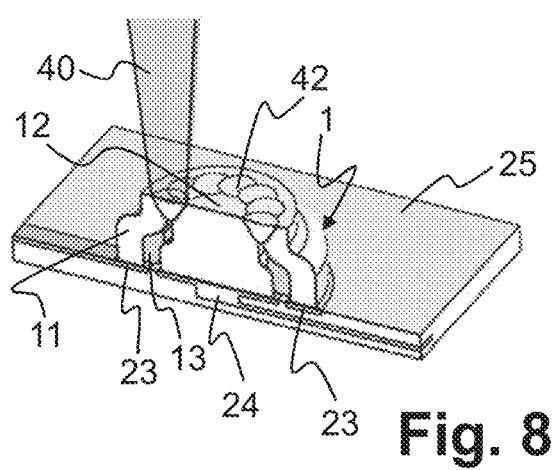

The plunger 12 has, in a central region, a sloped portion 19 relative to the height of the battery bridge 1 or the plunger 12, in which sloped portion the diameter of the plunger 12 changes from a smaller diameter to a larger diameter. The change in diameter lies, for example, in a range between 100 µm and 500 µm. A transition region or "kink" is thus formed to a certain extent in the plunger 12 in the sloped portion 19 and, as illustrated in FIG. 8, shields an electric circuit disposed therebeneath—here in the form of a printed circuit board 25—from the laser light of a laser beam 40, which is used for welding. Accordingly, the cap 11 can also have a sloped portion 20, and the ring 13 can have a sloped portion 21, wherein this portion 21 is arranged on the ring 13, as shown in FIG. 4, in the region of the upper side of the ring 13. This is provided on account of the arrangement of the ring 13 within the cap 11.

Figure 29:
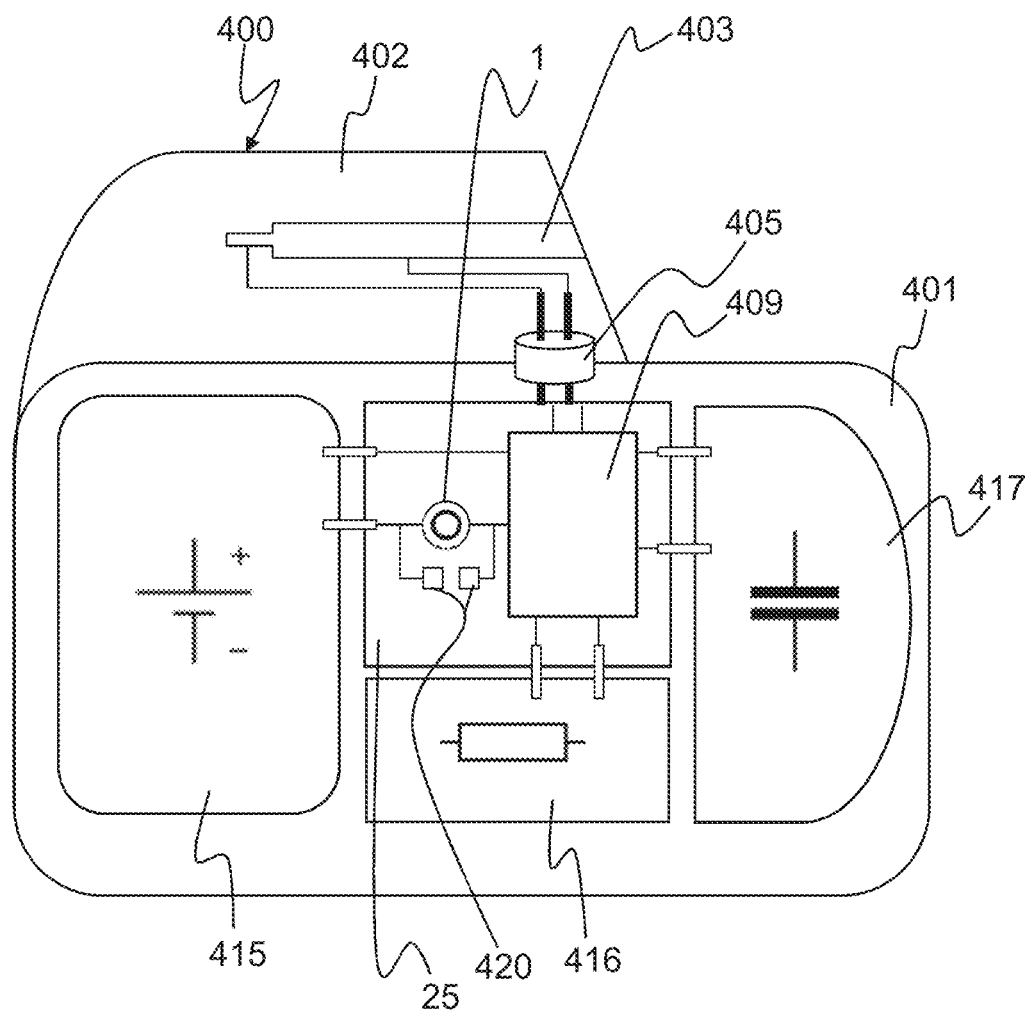

The method according to the present invention for activating an electronic device, for example, an electronic implant, by means of the battery bridge 1 according to FIG. 1 and a cardiac pacemaker 400 according to FIG. 29 as an example of an electronic implant will be explained hereinafter with reference to FIGS. 5-9 and 29.

The cardiac pacemaker 400 has an outwardly hermetically sealed housing 401 and a header 402 comprising a bushing 403 for producing the electrically conductive connection to electrodes (not illustrated). The electrical connection of contacts in the bushing to the printed circuit board (PCB) 25 arranged in the housing 401 and an IC (integrated circuit) 409 is established by means of a feedthrough 405, which is arranged between the header 402 and housing 401 and which is also hermetically sealed outwardly. As can be seen from FIG. 29, the IC 409 has electrically conductive connections to a battery 415, a dump resistor 416, and a capacitor unit 417 having a series of capacitors, wherein the battery 415, the dump resistor 416, and the capacitor unit 417 are arranged in the housing 401 of the cardiac pacemaker 400. In the electrical connection between IC 409 and the battery 415, the battery bridge 1 and test points 420 are arranged in parallel on the printed circuit board 25, in such a way that the electrical connection between the battery 415 and IC 409 is open, provided the battery bridge 1 is in the first (open) state.

The battery bridge 1 is produced in that the cap 11 and the plunger 12 are produced separately from one another, for example, by means of a cold forming or stamping process from a metal material. By way of example, the ring 13 is produced by means of plastics injection molding and, for example, consists of POM, PEEK, LCP and/or PBT. The ring 13 is then first arranged in the continuous opening 15 in the cap 11 and is pressed in, followed then by the plunger 12, such that a press fit is formed between the cap 11 and ring 13, and also between the ring 13 and plunger 12. The ring 13 thus positions the cap 11 and the plunger 12 concentrically with one another and the battery bridge 1 is in the first (open) state.

Figure 5:
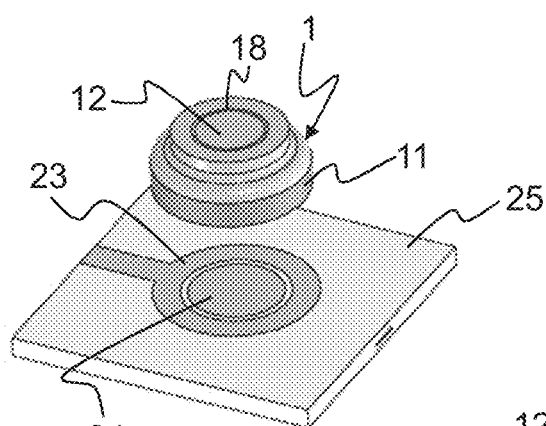
Figure 6:
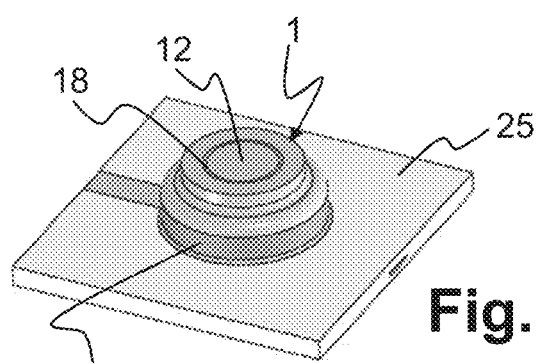

A battery bridge 1 produced in this way is now, as illustrated in FIGS. 5-6, arranged on a first contact face 23 or a second contact face 24 of the printed circuit board 25 and is electrically conductively connected thereto, for example, by means of soldering. For this purpose, a solderable coating (for example, containing at least one material of the group comprising gold, ENIG, EPIG (electroless palladium and immersion gold), palladium and tin) can be arranged, respectively, on the cap 11 or the plunger 12, on the lower end face 29 of the cap 11, in the lower region of the side face 30 of the cap 11, or on the lower region of the side face 33 of the plunger 12, and is applied prior to the assembly of the battery bridge 1. As a result of the soldering, the first contact face 23 is electrically conductively connected to the cap 11 and the second contact face 24 is electrically conductively connected to the plunger 12.

Once the cardiac pacemaker 400 has been produced with the electronic circuit, embodied at least in part as a printed circuit board 25, with the IC 409 and the battery bridge 1, and once all connections of the voltage source (battery 415) and of the capacitor unit 417 and of the dump resistor 415 have been connected to the circuit, preferably welded thereon, the circuit is initialized or powered up in a defined manner via the two test points 420 (power-up).

Figure 7:
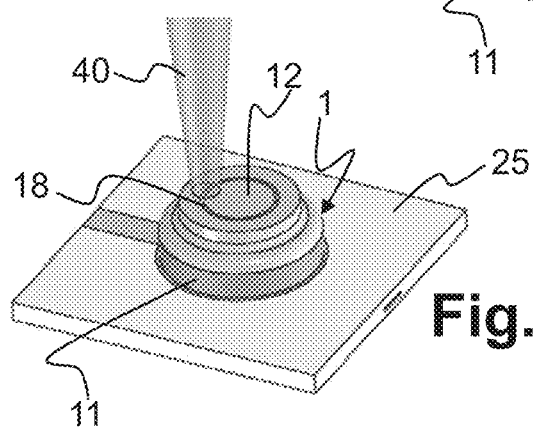
Figure 9:
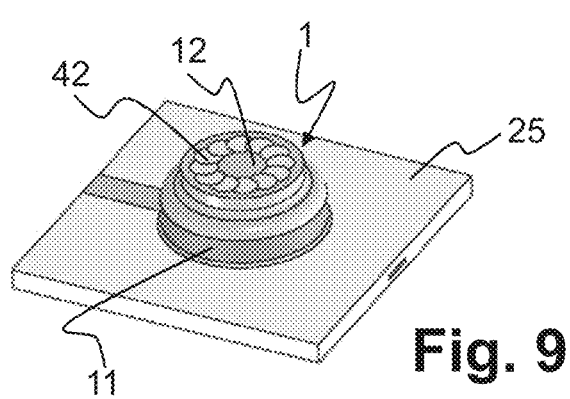
Figure 10:
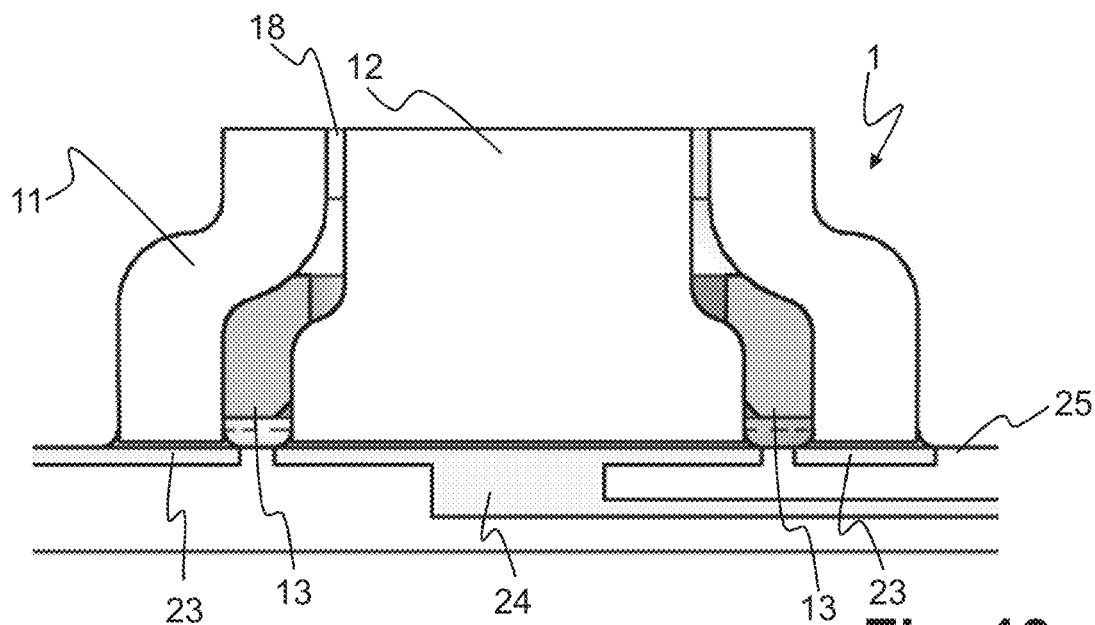
Figure 11:
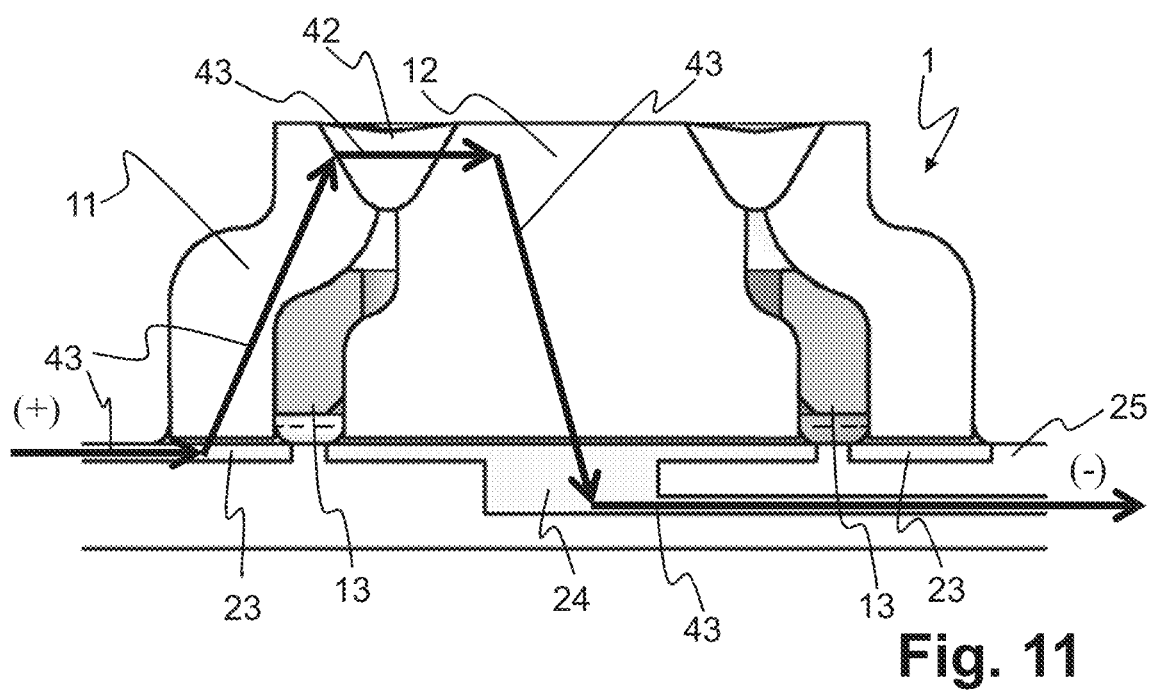

Following successful power-up, the cap 11 and the plunger 12 of the battery bridge 1 can then be used together in a single automatable process step by means of welding, for example, by means of laser welding, without further material feed or removal. This process step is shown in FIGS. 7-9. The laser beam 40 is for this purpose guided in the region of the end face 16 of the cap 11 along the air gap 18 and provides weld spots, such that in the region of the air gap 18 the material of the cap 11 and the material of the plunger 12 fuse with one another, form an electrically conductive connection between the cap 11 and plunger 12, and thus fill out the air gap 18 by a weld seam 42. The path of the electrons from a first conductive track with the first contact face 23 via the cap 11, the weld seam 42, the plunger 12 and the second contact face 24 of a second inductive track is illustrated by means of arrows 43 in FIG. 11. The circuit of the printed circuit board 25 is thus permanently closed, and the battery bridge 1 is in the second (closed) state.

In the first exemplary embodiment of a battery bridge 1 according to the present invention illustrated in FIGS. 1-11, the height of the cap 11 corresponds to the height of the plunger 12, such that the upper end face 34 of the plunger 12 runs flush with the end face 16 of the cap 11. By contrast, in the second exemplary embodiment of a battery bridge 1 illustrated in FIGS. 12-13, the height of the plunger 12 is greater than the height of the cap 11, such that the plunger 12 protrudes beyond the end face 16 of the cap. In this exemplary embodiment, the laser beam 40 can be positioned somewhat more easily, since it can be guided laterally of the plunger 12 along the air gap 18 (see FIG. 13). As a result of the welding, a fillet seam is formed in the region of the air gap 18 and electrically conductively connects the cap 11 to the plunger 12.

Figure 14:
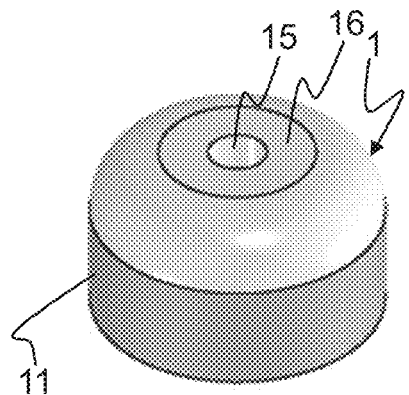
Figure 15:
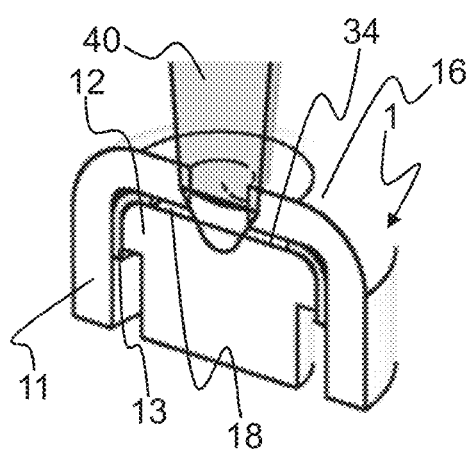

With regard to the first exemplary embodiment of a battery bridge 1 according to the present invention illustrated in FIGS. 1-11, in the third exemplary embodiment illustrated in FIGS. 14-15, the inwardly arranged plunger 12 now has a shorter height than the outwardly arranged cap 11. The cap has, in its end face 16, a continuous opening 15, through which the laser beam 40 is guided in order to achieve a connection between the material of the cap 11 and that of the plunger 12. The opening 15 in the cap 11 can also be replaced by a notch, i.e., can be closed at least in part, wherein welding is then performed through the notch in order to establish the electrically conductive connection to the plunger 12.

Figure 12:
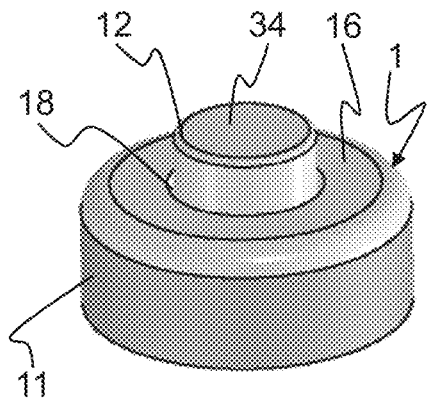
Figure 13:
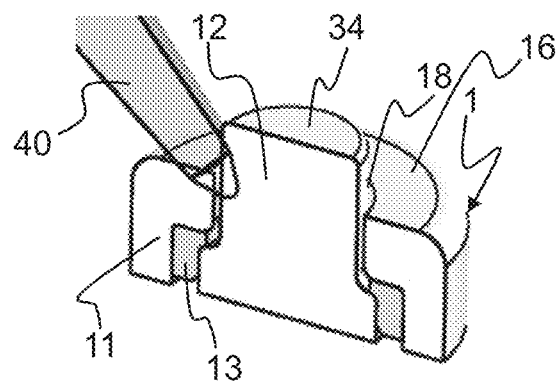
Figure 16:
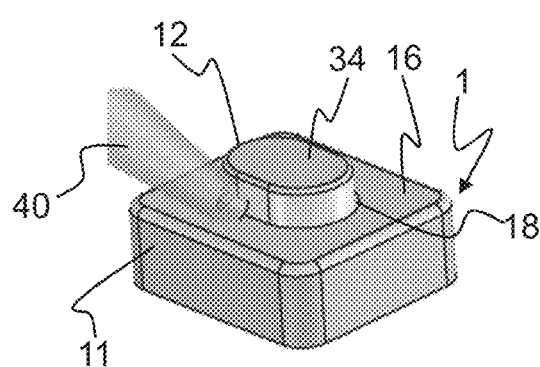
Figure 17:
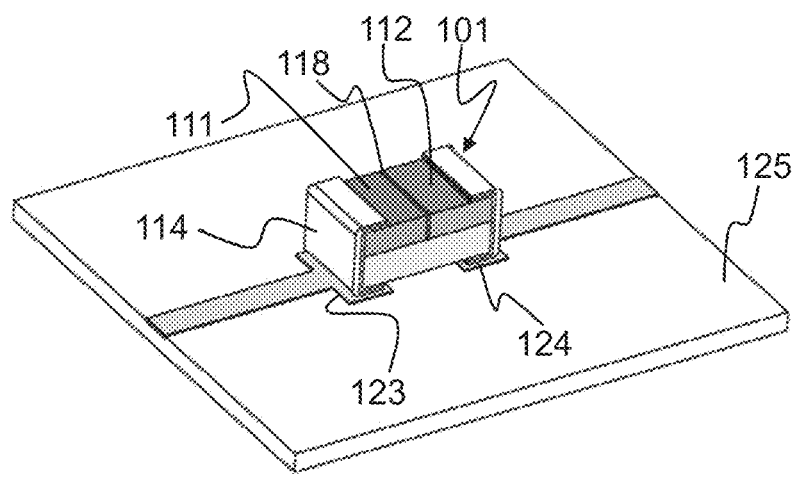
Figure 18:
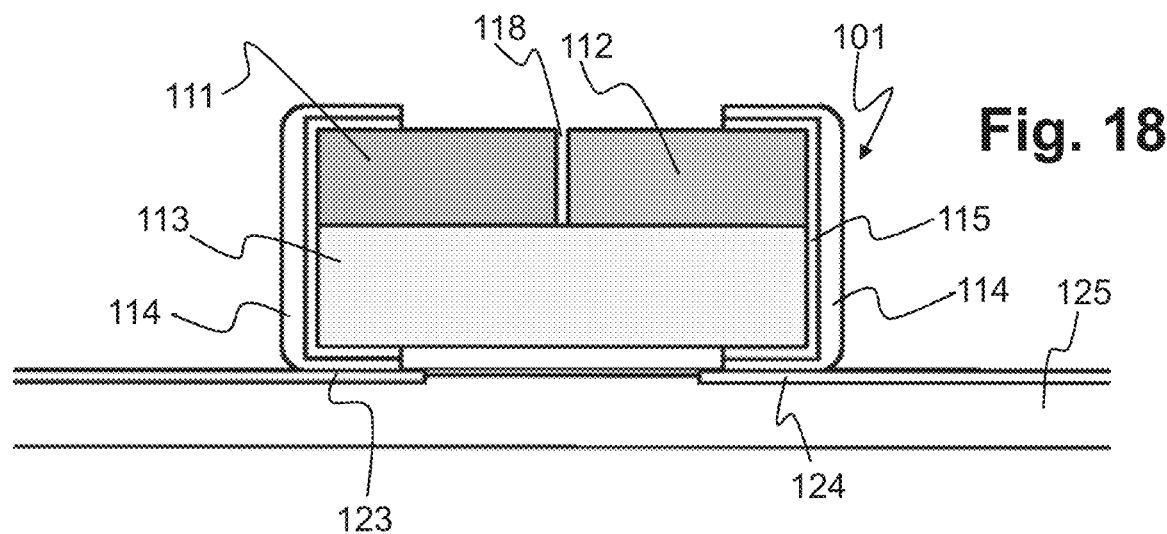

FIG. 16 shows a fourth exemplary embodiment of a battery bridge according to the present invention which is similar to the second exemplary embodiment according to FIGS. 12-13. The two exemplary embodiments differ from one another merely in the form of the cap 11, plunger 12 and/or ring (not illustrated) 13. Whereas these elements in the second exemplary embodiment according to FIGS. 12-13 are rotationally symmetrical, the cap 11 of the exemplary embodiment according to FIG. 16 has a non-symmetrical form, specifically a rectangular block form. Accordingly, the plunger also is not circular-cylindrical. The cross-sectional shape is essentially an ellipsis here. Accordingly, the insulator (not illustrated) also is not provided as a circular ring, but rather as an elliptical/rectangular ring. This exemplary embodiment has the advantage that the weld seam runs linearly, at least in part. Further forms are also conceivable for the cap 11, plunger 12 and ring 13 of the battery bridge.

Alternatively to the production of the contact elements by means of a cold forming or a punching process, a fifth exemplary embodiment of a battery bridge according to the present invention will be explained hereinafter on the basis of FIGS. 17-23, in which the components can be produced by means of thick-film technology, which constitutes an established, very efficient and economical technology.

The battery bridge 101 has a first weldable metal foil 111 (first contact element) and a second weldable metal foil 112 (second contact element), which are arranged adjacently on a ceramic substrate (insulator) 113, separated by an air gap 118. The thickness of the metal foils 111, 112 can be for example 400 µm, and the width of the air gap can be for example 50 µm. The metal foils 111, 112 can comprise, for example, nickel, copper, a copper-nickel alloy and/or stainless steel or can consist of one or more of these materials. By way of example, LTCC (low temperature co-fired ceramic) consisting of a number of materials (for example $SiO_2$, glass, titanate) or HTCC (high temperature co-fired ceramic with the primary component $Al_2O_3$) can be used as material for the ceramic substrate 113. A tin plating/soldering coating 114 (hereinafter soldering coating 114 for short) is arranged in each case laterally on the battery bridge 101 and on one side surrounds the first metal foil 111 and the ceramic substrate 113 in a U-shaped manner and on the other side surrounds the second metal foil 112 and the ceramic substrate 113 in a U-shaped manner. A nickel intermediate layer 115 is arranged between the soldering coating 104 and the metal foils 111, 112 and the ceramic substrate 114. As a result of the soldering coating 114 and the nickel intermediate layer 115, an electrically conductive connection is established from the metal foils 111, 112 to the underside of the ceramic substrate 113.

The method according to the present invention for activating an electronic device comprising a battery bridge 101 according to the present invention in accordance with the fifth exemplary embodiment is carried out similarly to the method explained with reference to FIGS. 5-9 and is illustrated in FIGS. 20-23. One difference lies merely in the fact that, in the case of the battery bridge 101, the contact elements 111, 112 are not directly connected to the contact faces 123, 124 of the printed circuit board 125, but instead the soldering coating 114 produces the electrical contact to the first metal foil 111 and second metal foil 112 arranged above the ceramic substrate 113.

Figure 22:
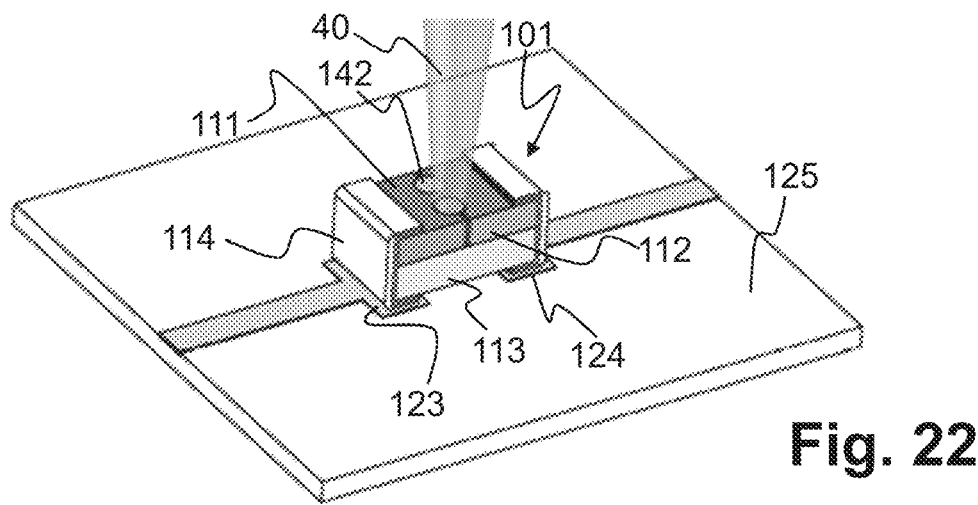
Figure 23:
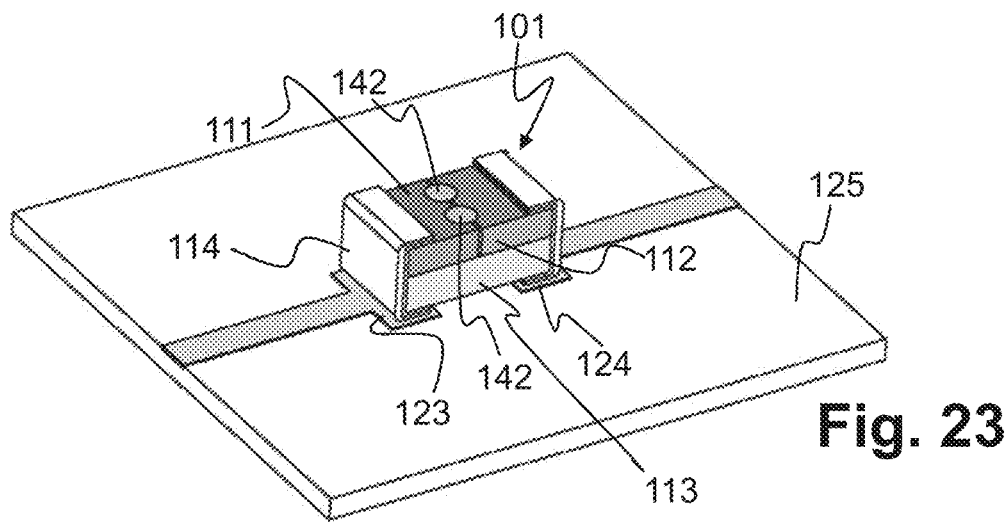

As illustrated in FIG. 22, in this method the first metal foil 111 additionally is not fused with the second metal foil 112 along the entire air gap 118, but instead merely two adjacently arranged weld spots 142 are provided along the air gap 118. Alternatively, just one weld spot can be provided, or more than two weld spots can be provided.

Figure 19:
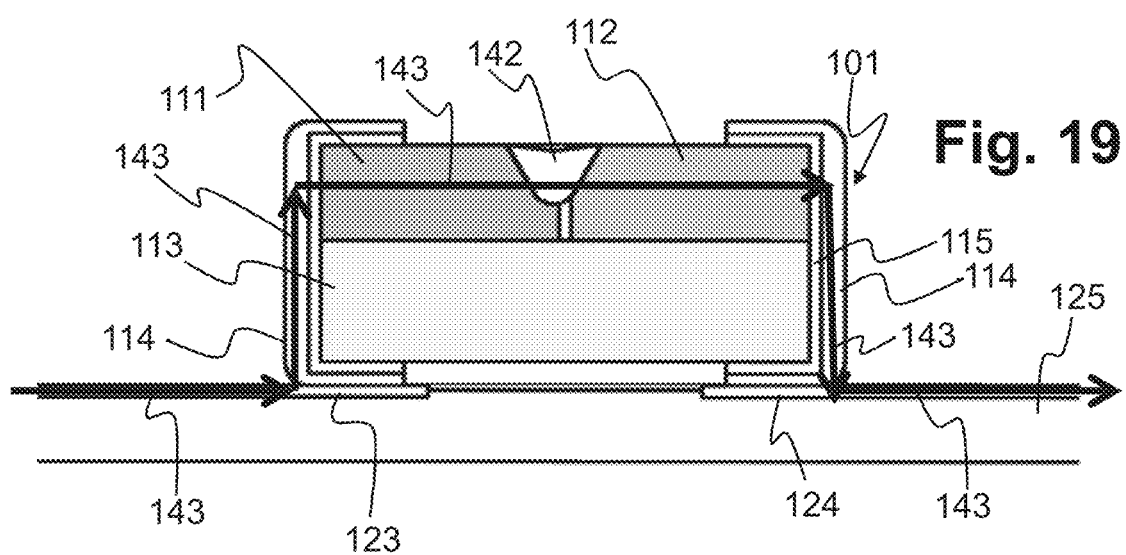
Figure 20:
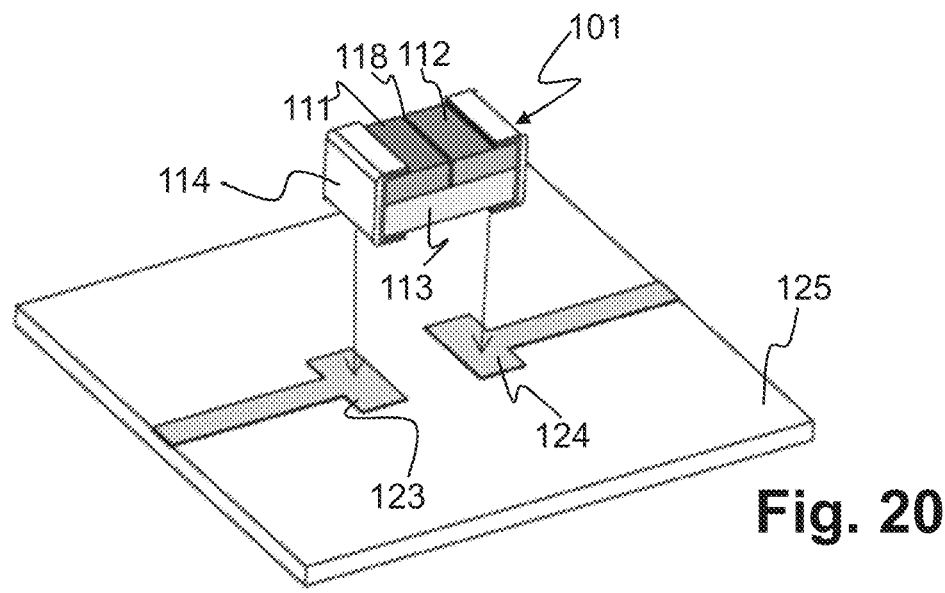
Figure 21:
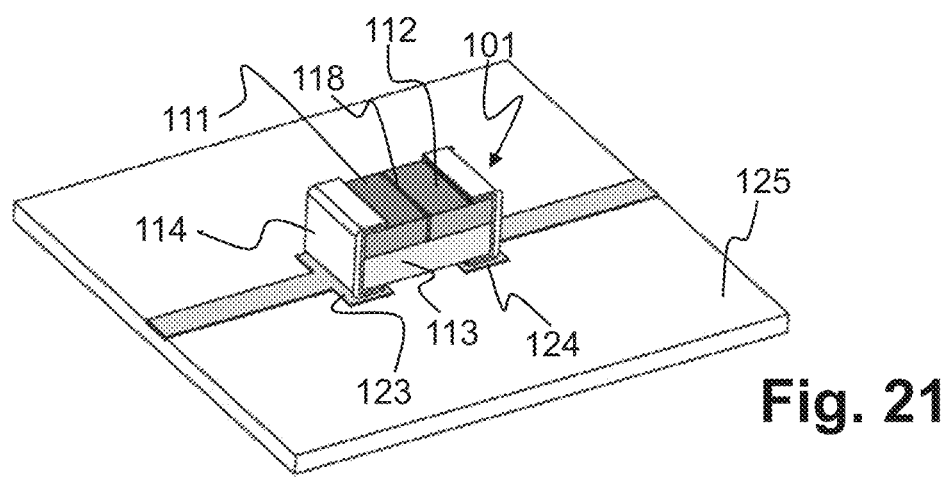

The path of the electrons along the conductive track with the first contact face 123, the soldering coating 114, the first metal foil 111, the weld point 142, the second metal coating 112, the soldering coating 114, and the conductive track with the second contact face 124 is indicated by means of arrows 143 in FIG. 19.

Figure 24:
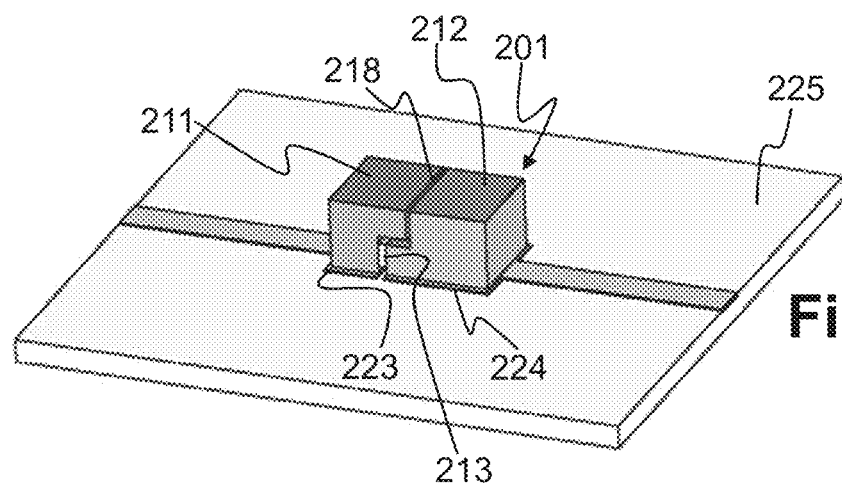
Figure 25:
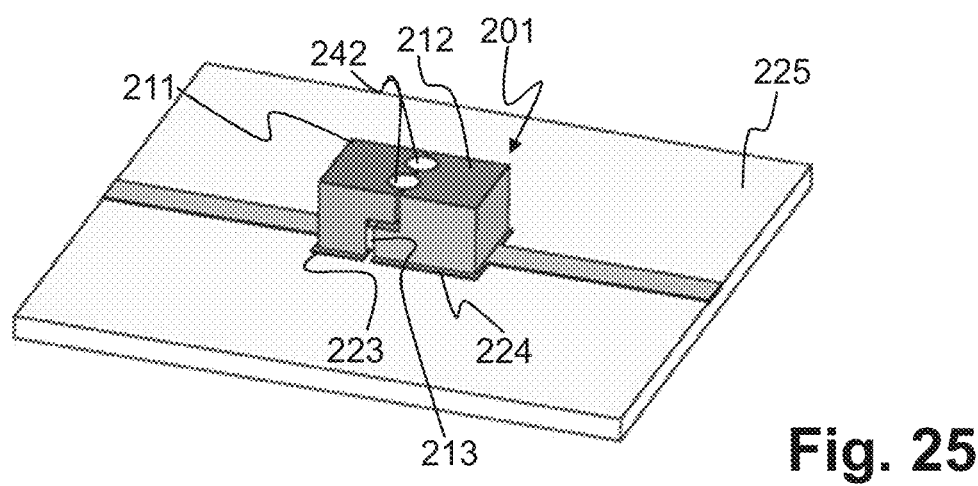

FIGS. 24-25 show a sixth exemplary embodiment of a battery bridge 201 according to the present invention. This has a first contact element 211, which is L-shaped in cross-section, and a second contact element 212, which is also L-shaped in cross-section. These complementary shapes are arranged in such a way that they supplement one another and form an air gap 218 between the first contact element 211 and the second contact element 212, more specifically between the opposing faces of these contact elements 211, 212. The air gap 218 accordingly forms a step shape. An insulator 213 in the form of an adhesive film is arranged in a lower region of the air gap 218 and by way of example is strip-like. The contact elements 211, 212 are preferably produced by means of cold forming, MIM (metal injection molding), milling, or etching, and the insulator 213 is produced from an acrylate adhesive film. The arrangement on a printed circuit board 225 having a first contact face 223 and a second contact face 224 is provided in such a way that the first contact element 211 is directly soldered to the first contact face 223 and the second contact element 212 is directly soldered to the second contact face 224. Similarly to the exemplary embodiment of the battery bridge 111, a connection of the two contact elements 211, 212 and the second (closed) state of the battery bridge 201 is achieved by two weld spots 242.

Figure 26:
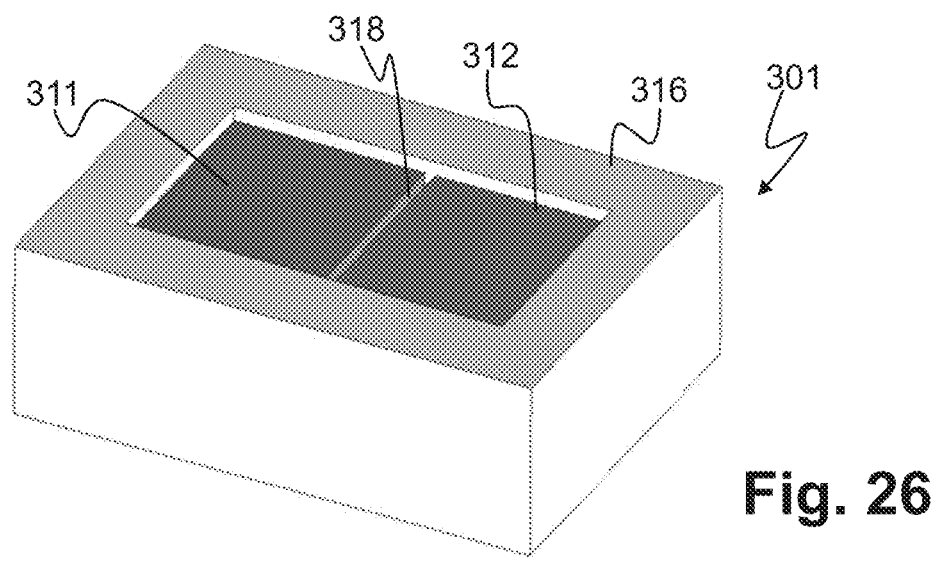
Figure 27:
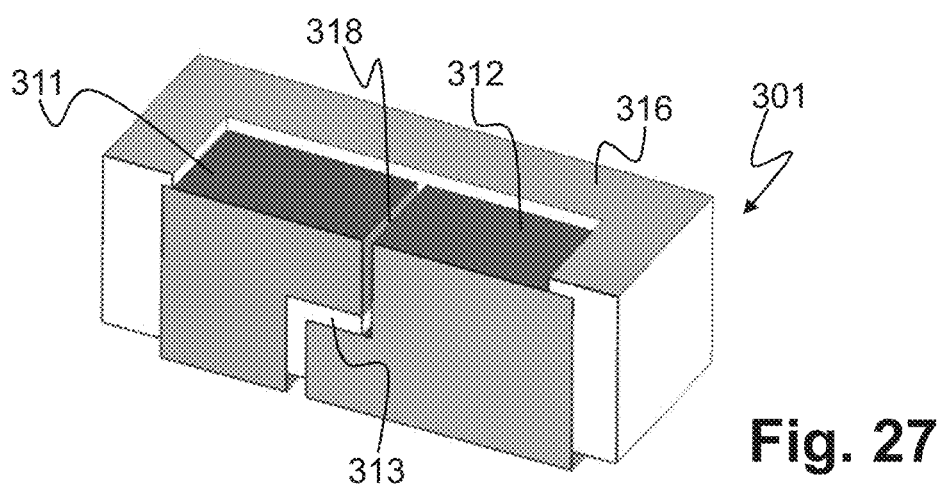
Figure 28:
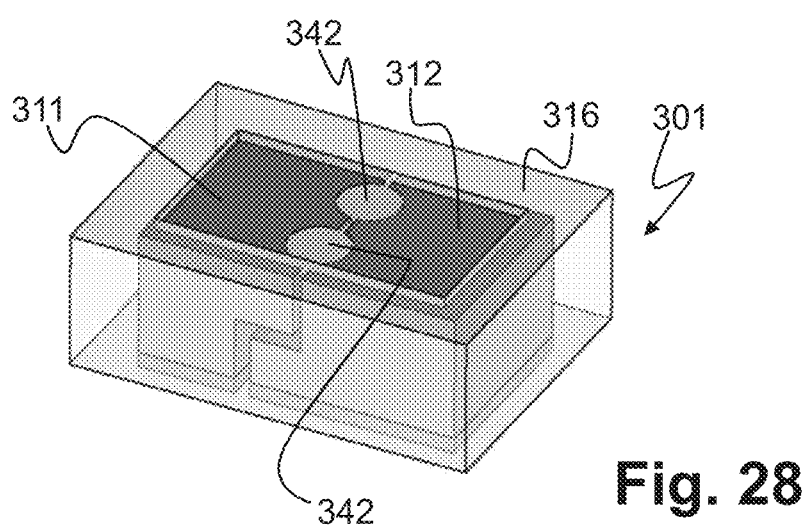

The seventh exemplary embodiment of a battery bridge 301 according to the present invention illustrated in FIGS. 26-28 is similar in terms of structure to the battery bridge 201 illustrated in FIGS. 24-25. The first contact element 311 and the second contact element 312 also each have a complementary form that is L-shaped in cross-section, but in which an air gap 318 is formed. The insulator 313, formed, for example, as an adhesive film, also has here a strip shape in cross-section, preferably with a step. The battery bridge 301 also has a rectangular annular housing 316, which annularly surrounds the first contact element 311 and the second contact element 312. The first contact element 311 and the second contact element 312 protrude beyond the housing 316 on the underside so as to be able to establish proper contact with corresponding contact faces of a printed circuit board. In the closed state of the battery bridge 311 illustrated in FIG. 28, the first contact element 311 and the second contact element 312 are electrically conductively connected to one another via weld spots 342.

The advantages of the above-presented SMT-capable battery bridges 1, 101, 201, 301 according to the present invention and the above-explained method according to the present invention for activating an electronic device lie in particular in the ability to automate the initialization and closing process of the circuit. A greater process reliability and a reduction of the run-through time for the power-up can thus be achieved. It is not necessary to remove material and it is also not necessary to hold down contacts. With a battery bridge 1, 101, 201, 301 that can be welded in an automated manner in accordance with the present invention, the manufacturing flow can be significantly simplified.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMERALS

1 battery bridge
11 cap (first contact element)
12 plunger (second contact element)
13 ring (insulator)
15 opening
16 upper end face of the cap 11
18 air gap
19 portion
20 portion
21 portion
23 first contact face of a conductive track
24 second contact face of a conductive track
25 printed circuit board
29 lower end face of the cap 11
30 side face of the cap 11
32 lower end face of the plunger 12
33 side face of the plunger 12
34 upper end face of the plunger 12
40 laser beam
42 weld seam
43 arrow
101 battery bridge
111 metal foil (first contact element)
112 metal foil (second contact element)
113 ceramic substrate (insulator)
114 tin plating/soldering coating
115 intermediate layer
118 air gap
123 first contact face of a conductive track
124 second contact face of a conductive track
125 printed circuit board
142 weld spot
143 arrow
201 battery bridge
211 first contact element
212 second contact element
213 insulator
218 air gap
223 first contact face of a conductive track
224 second contact space of a conductive track
225 printed circuit board
242 weld spot
301 battery bridge
311 first contact element
312 second contact element
313 insulator
316 housing
318 air gap
342 weld spot
400 cardiac pacemaker
401 housing
402 header
403 bushing
405 feedthrough
409 IC
415 battery
416 dump resistor
417 capacitor unit
420 test point

I claim:

1. A battery bridge for an electronic device, preferably, for an electronic implant, comprising:
   an electrically conductive first contact element;
   an electrically conductive second contact element; and
   an insulator, wherein the first contact element and the second contact element comprise a weldable material, wherein, in a first state of the battery bridge, the first contact element is distanced from the second contact element via a predefined air gap and the first contact element is electrically insulated from the second contact element by the air gap and the insulator, wherein the battery bridge is configured in such a way that it can be transferred, by welding the first contact element and the second contact element to one another, into a second state, in which the air gap between the first contact element and the second contact element is closed electrically conductively, at least in part.

2. The battery bridge according to claim 1, wherein the insulator is substantially annular, the first contact element is substantially U-shaped or hollow cylindrical in cross-section, and the second contact element is substantially cylindrical, wherein the annular insulator is arranged between the first contact element and the second contact element.

3. The battery bridge according to claim 2, wherein the second contact element is arranged within an inner opening of the first contact element, which opening is preferably continuous.

4. The battery bridge according to claim 2, wherein the second contact element has a sloped portion, which shields an electric circuit arranged beneath the battery bridge from a laser light used for welding.

5. The battery bridge according to claim 2, wherein the first contact element and/or the second contact element has, in a portion serving for connection to the electric circuit, a coating which improves solderability.

6. The battery bridge according to claim 2, wherein the second contact element, in the region of an upper end face of the first contact element, in which region the welding is performed, protrudes beyond this upper end face.

7. The battery bridge according to claim 1, wherein the insulator is formed as a ceramic substrate and the first contact element is formed as a first metal foil and the second contact element is formed as a second metal foil, wherein the first contact element and the second contact element are arranged on the insulator at a distance corresponding to the width of the air gap.

8. The battery bridge according to claim 1, wherein the first contact element has a first shape and the second contact element has a second shape, which is complementary to the first shape, wherein the air gap is formed at the opposing faces of the first shape and the second shape and in a region is filled out by the insulator, which is formed for example as an adhesive film.

9. The battery bridge according to claim 1, wherein the air gap has a width ranging from 10 μm to 100 μm.

10. The battery bridge according to claim 1, wherein the air gap has a width ranging from 30 μm to 80 μm.

11. A method for activating an electronic device, preferably an electronic implant, comprising an electric circuit by means of a battery bridge according to claim 1, comprising the following steps:
- positioning and fastening the battery bridge in the first state on the electric circuit and producing an electrically conductive connection between the first contact element and a first conductive track and between the second contact element and a second conductive track of the electric circuit;
- connecting the electric circuit to a voltage source and/or a capacitor and/or a dump resistor;
- powering up the electric circuit via at least two predefined test points; and
- transferring the battery bridge into the second state by at least partially welding the first contact element and the second contact element to one another, in such a way that the air gap is electrically conductively closed, at least in part.

12. The method according to claim 11, wherein a butt seam welding method or a fillet welding method or a through-welding method is used for welding.

* * * * *